United States Patent [19]

Zakaryan

[11] 4,035,449
[45] July 12, 1977

[54] PROCESS FOR THE PRODUCTION OF S-ALKYL PHOSPHORO DIHALOGENIDODITHIOATE

[75] Inventor: Ara Zakaryan, Shawnee Mission, Kans.

[73] Assignee: Mobay Chemical Corporation, Pittsburgh, Pa.

[21] Appl. No.: 625,345

[22] Filed: Oct. 23, 1975

[51] Int. Cl.$^2$ .......................................... C07F 9/20
[52] U.S. Cl. ............................... 260/972; 260/948; 260/950; 260/958; 260/960; 260/985
[58] Field of Search .................... 260/972, 985, 960

[56] References Cited

U.S. PATENT DOCUMENTS

| | | | |
|---|---|---|---|
| 2,943,107 | 6/1960 | Rattenbury et al. | 260/972 |
| 3,457,306 | 7/1969 | Baker et al. | 260/543 |
| 3,879,500 | 4/1975 | Uhing et al. | 260/960 X |

OTHER PUBLICATIONS

Houben–Weyl, Methoden der Organischen Chemie, 12/2, (1964), pp. 682, 683, 739 and 740.

*Primary Examiner*—Richard L. Raymond
*Attorney, Agent, or Firm*—Gene Harsh; Lawrence S. Pope

[57] ABSTRACT

S-alkyl phosphoro dihalogenidodithioate is prepared by the reaction of alkyl mercaptan with a phosphorous trihalogenide ($PX_3$) and elemental sulfur in the presence of a sulfurization catalyst. The alkyl mercaptan may be reacted with the phosphorous trihalogenide either in a separate vessel or in the same vessel as the subsequent sulfurization of these reaction products. Sufficient sulfur is used to sulfurize substantially all phosphorous atoms present to a penta-valent state. If a sufficient excess of phosphorous trihalogenide is not used in the initial reaction either additional phosphoroustrihalogenide or $PSX_3$ is added so that at the end of sulfurization there is at least about one mole of $PSX_3$ present for each mole of S,S-dialkyl phosphorohalogenido trithioate and two moles for each mole of S,S,S-trialkyl phosphorotetrathioate present. The $PSX_3$ and dialkyl and trialkyl compounds are held at sufficient temperature for a sufficient time to convert them substantially to S-alkyl phosphorodihalogenidodithioate. A period of at least about 1 hour at not less than about 150° C is preferred. The $PSX_3$ and product (S-alkyl phosphorodihalogenidodithioate) may be removed as distillation overheads and the residue left as a heel for subsequent cycles.

9 Claims, No Drawings

PROCESS FOR THE PRODUCTION OF S-ALKYL PHOSPHORO DIHALOGENIDODITHIOATE

FIELD OF THE INVENTION

This invention relates to the production of S-alkyl phosphorodihalogenidodithioate from phosphorous trihalogenide, alkyl mercaptans and elemental sulfur.

BACKGROUND OF THE INVENTION

S-alkyl phosphorodihalogenidodithioate are known compounds which find utility as intermediates for the production of compounds which exhibit biocidal properties, particularly insecticidal and herbicidal properties.

A number of processes for the production of S-alkyl phosphorodichloridodithioate are known and some of them are reviewed in U.S. Pat. No. 3,879,500 and in greater detail in Methoden Der Organishen Chemie Band XII/2, Thiel 2 — pages 682–683 and 739–740 (1963) published by Georg Thieme Verlug; Stuttgart Germany. The present process is believed to produce better yields in shorter times and at lower temperatures.

The reaction of alkyl mercaptans with phosphorous trichloride to yield S-alkyl phosphoro dichloridothioate is known. The reaction of phosphorodichloridothioate with elemental sulfur to yield S-alkyl phosophorodichloridodithioate is known. Finally, the reaction of S-alkyl phosphorochloridotrithioate with S,S-dialkyl phosphorothiotrichloride to yield S-alkyl phosphorodichloridodithioate is disclosed in U.S. Pat. No. 3,879,500. However, there is no teaching of a combination of these steps into a process which can produce S-alkyl phosphorodihalogenidodithioates in high yields of over 80% in short production times of under 8 hours.

It is therefore an object of the present invention to provide a method of producing high yields in short times of S-alkyl phosphorodihalogenidodithioates. It is a further object to provide such a method wherein the starting materials are readily available.

The most recent process for the production of S-alkyl phosphorodichloridodithioate, taught in U.S. Pat. No. 3,879,500, requires at least 13 hours to achieve net yields of less than 70%. These results are reported for S-methyl phosphorodichloridodithioate and the other results reported indicate much less satisfactory results are achieved with higher alkyl groups.

SUMMARY OF THE INVENTION

The present invention involves a process of producing S-alkyl phosphorodihalogenidodithioates from alkyl mercaptan with a phosphorous trihalogenide and elemental sulfur in the presence of a sulfurization catalyst. The reaction sequence is believed to be as follows:

I $PX_3 + RSH \longrightarrow RSPX_2 + (RS)_2PX + (RS)_3P + HX$ wherein R is a lower alkyl and X is Cl, Br or I, preferably Cl or Br, most preferably Cl II $RSPX_2 + (RS)_2PX + (RS)_3P + S \xrightarrow{\text{catalyst}}$

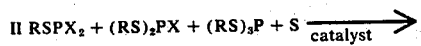

III 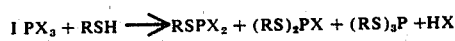

The $PSX_3$ can either result from an excess of $PX_3$ in reaction I which is sulfurized in reaction II or it can be a deliberate addition of either $PX_3$ to reaction II or $PSX_3$ to reaction III. All three reactions can take place in a single vessel or reaction I can take place in a separate vessel. The process can also be practiced in a continuous manner, e.g., in a tube reactor, provided zones with the appropriate reaction conditions are provided. The order of addition of reactants is immaterial. However, it is preferred to add the mercaptan to the $PX_3$ to avoid loss of mercaptan with evolved HX.

The proportion of each of the products of reaction I is controlled by the reaction temperature and the ratio of the trihalogenide to mercaptan. Higher temperatures and lower ratios favor the formation of di- and trialkyl products. The sulfurization reaction (II) usually requires the presence of a catalyst to ensure that all the trivalent phosphorous present is converted to the penta-valent state. About one mole of $PSX_3$ is required to convert each mole of the di- or each half mole tri-alkyl, products to the monoalkyl product. The monoalkyl product (S-alkyl phosphorodihalogenidodithioate) may be separated from the unconverted dialkyl and trialkyl product and other reaction residue by distillation or other physical separation means such as filtration or crystallization. The dialkyl or trialkyl products may be recycled and participate with subsequently formed products in reaction III.

This method can achieve net yields of greater than about 80% and can be run in less than about 8 hours.

DETAILED DESCRIPTION OF THE INVENTION

The mercaptan compound used as a starting material in the present invention has the general formula:

RSH         (1)

wherein R is a straight chained or branched alkyl with up to 15 carbon atoms optionally substituted with halogen, alkoxy or alkylthio or cycloalkyl with 5 to 6 ring carbons, preferably an unsubstituted $C_1$–$C_6$ alkyl and most preferably n-propyl. Compounds which can be produced by the process of the present invention include:

S-methyl dichlorophosphorodithioate
S-ethyl dichlorophosphorodithioate
S-propyl dichlorophosphorodithioate
S-butyl dichlorophosphorodithioate
S-pentyl dichlorophosphorodithioate
S-hexyl dichlorophosphorodithioate
S-isopropyl dichlorophosphorodithioate
S-iso-butyl dichlorophosphorodithioate
S-sec-butyl dichlorophosphorodithioate
S-tert-butyl dichlorophosphorodithioate
S-2-methyl-1-butyl dichlorophosphorodithioate
S-iso-amyl dichlorophosphorodithioate
S-neopentyl dichlorophosphorodithioate
S-2-pentyl dichlorophosphorodithioate
S-3-methyl-2-butyl dichlorophosphorodithioate
S-tert-amyl dichlorophosphorodithioate S-2-methyl-1-pentyl dichlorophosphorodithioate
S-3-methyl-1-pentyl dichlorophosphorodithioate
S-isohexyl dichlorophosphorodithioate
S-2-ethyl-1-butyl dichlorophosphorodithioate and other branched S-hexyl dichlorophosphorodithioates.

The proportion of dialkyl and trialkyl products which result in reaction I depends upon the temperature of the reaction and the ratio of trihalogenide to mercaptan. As the temperature is increased the proportion of dialkyl and trialkyl products increases. It is preferred that the temperature of reaction I be no more than about 50° to 75° C, and particularly preferred that it be no more than about 35° C. As the ratio of trichloride to mercaptan is increased the proportion of monoalkyl product increases. At least about a molar equivalent of trichloride to mercaptan is preferred and a molar ratio of 3:1 is especially preferred. A 1:1 molar ratio of trihalogenide to mercaptan can yield about a 2:1 mix of mono- and dialkyl product while a 3:1 ratio can yield a 15:1 mix.

Normally this reaction requires temperatures in excess of about 50° C. However, in the presence of the residue of reactions II and III, particularly the sulfurization catalyst, this reaction will occur at room temperature (20° C) or lower. Also, in the absence of this catalysis the reaction usually requires at least about an hour to complete while even at room temperature or lower the catalyzed reaction proceeds essentially instantaneously. The only limitation is the ability to dispose of the evolved HX. The course of this reaction can be monitored either catalyzed or uncatalyzed by the HX evolution. When the evolution ceases the reaction is essentially complete.

It is preferred to use enough elemental sulfur in the sulfurization reaction to convert substantially all the trivalent phosphorous compounds present to the penta-valent state. In the penta-valent state, the monoalkyl compounds are more stable than in the trivalent state. It appears that the equilibrium reverses on sulfurization and that higher temperatures favor the formation of monoalkyl over dialkyl and trialkyl. In practice, it may be advantageous to use an excess of sulfur in the first cycle to condition the catalyst. An excess of at least 20 mol% is preferred and an excess of 50 mol% is especially preferred.

The sulfurization of the trivalent phosphorous compounds to the penta-valent state reaction (II) should take place in the presence of a catalyst. Any catalyst which promotes the sulfurization of phosphorous compound is suitable. Preferred catalysts are activated carbon and dimethyl formamide, with the activated carbon being especially preferred.

The catalyst should be present in an effective amount. At least about 0.5 g per equivalent of trivalent phosphorous is preferred with about 5.0 or more g per equivalent being particularly preferred.

The trivalent phosphorous compounds and the elemental sulfur are heated to a temperature of at least about 85° C, preferably about 125° C to initiate the sulfurization reaction. The temperature may then increase somewhat from the sulfurization reactions. The conversion of $PX_3$ to $PSX_3$ is particularly exothermic. This heat and external heat may be used to reach a temperature of at least about 130° C, preferably 150° C. At this temperature reaction III will proceed. It is preferred to initially heat the reactants to a temperature of about at least 150° C as soon as possible and hold them at this temperature until reaction III is substantially complete, i.e., the reactants are in equilibrium with the products for the reaction conditions. This can occur in as little as one hour. It is preferred not to raise the temperature significantly above 150° C. in order to avoid loss of the $PX_3$ and $PSX_3$ which both have high vapor pressures.

The process of the present invention can be carried out at pressures from sub- to super- atmospheric. However, it is preferred that at least reaction I be carried out at pressures no greater than atmospheric to aid in the elimination of any HX formed by vapor expiration and minimize the chance of atmospheric odor pollution. On the other hand, pressures too much below atmospheric should be avoided or a loss of reactants to the vacuum system may result. The $PX_3$ and $PSX_3$ are especially susceptible to loss by vaporization. In addition to the loss of the reactants per se, a loss of a substantial amount of material will also result in a loss of heat. It may in some cases be advantageous to run reactions II and III at super-atmospheric pressure in order to achieve or maintain desired reaction temperatures. For ease of operation and minimal economic cost, it is preferred to run the process at atmospheric pressure.

The final desired product, S-alkyl phosphorodihalogenidodithioate, may be recovered by vacuum distillation after the substantial completion of reaction III. However, because it has a higher vapor pressure it is necessary to distill off any $PSX_3$ present first. The residue will consist of unconverted di- and trialkyl pentavalent esters, reaction by products such as dialkyldisulphide and the sulfurization catalyst.

In a preferred embodiment of the present invention, the residue left after the distillation of both the monoalkyl product and the $PSX_3$ is recycled to the next cycle. In one embodiment this means in effect that the residue is left in the vessel and fresh trivalent phosphorous compounds and elemental sulfur is charged into the vessel. If activated carbon is the catalyst, it may also be left in the vessel. The distilled $PSX_3$ may then be reintroduced into the vessel. In a particularly preferred embodiment the entire process takes place in a single vessel. In this case the alkyl mercaptan and $PX_3$ are initially charged into the vessel containing the residue. After the substantial completion of reaction I sulfur and $PSX_3$ distilled from the previous cycle are introduced into the vessel.

In one preferred embodiment the mercaptan is initially reacted with the phosphorous trihalogenide until substantially all of the mercaptan is converted to trivalent phosphorous thioesters. A temperature of between about 50° to 75° C for between about 1 and 4 hours is preferred for this reaction. In a further preferred embodiment the $PX_3$ still present is stripped by vacuum distillation from the reaction mixture. The amount of dialkyl and trialkyl thioesters $((RS)_2PX)$ and $(RS_3)P$ present in the reaction mixture is determined. This reaction mixture, elemental sulfur, a sulfurization catalyst and $PSX_3$ is then charged into a second reaction vessel. Sufficient sulfur is charged to convert all the trivalent phosphorous present to the penta-valent state. Initially sulfur in excess of the molar amount of trivalent phosphorous compound should be charged. However, in subsequent cycles a molar equivalent may be sufficient. Enough $PSX_3$ should be charged to provide at least a mole for each mole of $(RS)_2PSX$ and two moles for each mole of (RS)₃P. Some or all of the PSX₃ may be supplied by carrying over unreacted PX₃ from the first reaction. But it is preferred not to charge substantial quantities of PX₃ to this sulfurization reaction because its sulfurization of PSX₃ is highly exothermic and the heat generated makes temperature control more difficult. This vessel is cooked at a sufficient temperature for a sufficient time to ensure that substantially all the trivalent phosphorous present is converted to the pentavalent state and that the major portion of the final product is the monoalkyl thioester

(RSPX₂).

A cook temperature of at least about 150° C for at least about 1 hour should give yields of in excess of about 80%

RSPX₂ based on the mercaptan initially charged after the first cycle. The PSX₃ is then removed by vacuum distillation and may be recycled to the next cycle. The cycle is completed by the vacuum distillation of the S-alkyl phosphorodichloridodithioate

(RSPX₂).

The distillation residue is then used as a heel in the next cycle sulfurization. The process is then repeated for numerous cycles in each case using the previous cycles distillation residue as a heel in the sulfurization reaction. The presence of this heel appears to significantly improve the recovery of S-alkyl phosphorodihalogenidodithioate.

In another preferred embodiment both the mercaptan halide reaction and the sulfurization reaction are carried out in a single vessel. In this embodiment it is preferred to either use no more than about 1 molar equivalent of PX₃ based on the mercaptan or to strip the PX₃ present after the first reaction. This avoids sulfurization of substantial quantities of PX₃ which is undesirable for reasons already discussed. After the completion of the first reaction and the PX₃ stripping the appropriate amounts of sulfur and sulfurization catalyst and PSX₃ are charged and the process proceeds in much the same manner as in the two vessel embodiment.

In both embodiments if a sulfurization catalyst is used which is not removed by the vacuum distillation of either the PSX₃ of the

RSPX₂ it need not be added after the first cycle. Activated carbon is such a catalyst. When the carbon catalyst is fresh it is advantageous to charge sulfur on excess of that needed to sulfurize the phosphorous present. An excess of at least about 20 mol% is preferred, most preferably 50 mol%.

In the later embodiment the mercaptan halide reaction may be completed before the addition of the elemental sulfur and PSX₃ or all the reactants may be added initially. In the later case it is preferred to add the mercaptan last to avoid its loss with HX evolution.

In general, it is preferred that reaction III take place in the presence of the products of reaction II and the sulfurization catalyst, particularly the catalyst. It is believed that this catalyst also catalyzes reaction III and that the sulfurization products may have some additional catalytic effect on reaction III.

It is also preferred that reaction II take place in the presence of the residue of a previous cycle, i.e., the by products of reaction III from which the product (monoalkyl thioester) has been removed. It is believed that the presence of di- and trialkyl thioesters from a previous cycle improves the yield of a given cycle.

Finally, it is preferred that reaction I take place in the presence of the sulfurization catalyst. It is believed that this catalyst also catalyzes reaction I. It is particularly preferred to use activated carbon for this dual purpose.

EXAMPLES

EXAMPLE 1

Preparation of PrSPCl₂

Equipment — 250 ml, 3 necked flask; dry ice condensor; thermometer; 1 addition funnel; 1 heating mantel Equation $PCl_3 + PrSH \longrightarrow PrSPCl_2 + HCl$ phosphorous trichloride (MW 137) + propyl mercaptan (MW 76) ⟶ S-n-propyl phosphorodichloridothioite (MW 177)

Charge

| PCl₃ | 205.5 g | 0.5 m + 200% excess |
| --- | --- | --- |
| PrSH | 38 g | 0.5 mole |

Procedure

Flask charged with PCl₃, agitation started, heated to 50° C, and PrSH added through addition funnel at 50° C–55° C. Following addition, the mixture cooked 4 hours at 75° C.

Following cook period, the mixture transferred to aspirator volume to strip off PCl₃. The stripped material was then placed on gas liquid chromatograph (GLC) and a crude, A.I., net was calculated with the following results:

crude (yield) — 82.3 g/88.5 g = 93% crude
A.I. — 93.7 %
net yield — 87%

EXAMPLE 2

Sulfurization of PrSPCl₂

Equipment — 500 ml flask, stirrer, thermometer, condensor and heat mantle

Equation- $PrSPCl_2 + S \xrightarrow[PSCl_3, heat]{C} PrSPCl_2$
(177)   (32)                         (209)

Raw Materials

| 88.5 g | PrSPCl₂ | (0.5 mole) |
| --- | --- | --- |
| 24.0 g | Sulfur | (0.5 mole + 50% X S) |
| 7.0 g | C | (14 g/mole) |
| 17.0 g | PSCl₃ | (0.1 mole) |

Procedure

Charge all of the above and heat to 145° C and cook 3 hours. Distill each at 1.5 mm Hg.

```
1st cut = 26.8 g        (theoretical)
Prod. Cut = 70.3 g      ──── 104.5 g = 67.3% crude distilled
A.I. = 91.3%
Net Yield (by normalization) = 61.4%
```

EXAMPLE 3

Production of PrSPCl$_2$ in presence of activated carbon and subsequent sulfurization 1. 144.4 lb (1.046 moles) of PCl$_3$ was charged to a 50 gallon reaction vessel. Fifteen pounds of activated carbon was then added with stirring. Then 80 pounds (1.0506 moles) of PrSH (n-propyl mercaptan) were added at a temperature of 17 to 20° C over a period of 1.17 hours. HCl evolution was instantaneous with the mercaptan addition and ceased as soon as the addition was complete. The vessel was then heated to 70° C to drive off any HCl present and cooled to 40°–50° C.

2. Then 51.0 pound (1.5938 moles) of sulfur was added followed by 52.5 lb (0.3097 moles) of PSCl$_3$. The vessel was heated to 100° to 110° C and gradually heated until reflux ceased.

3. The vessel was then heated to 150° to 155° C and cooked for 2½ hours.

4. The vessel was cooled to 50° C or less.

5. PSCl$_3$ was vacuum distilled from the vessel.

6. PrSP(S)Cl$_2$ was vacuum distilled at 5 mm until the vessel temperature reached 125° C.

7. The crude yield based upon theoretical possible net amount of product was 58.92% (129.4 lbs. of crude product recovered/209 lbs. possible yield). The crude product had 95.31% active ingredient to give a net yield of 56.17%.

EXAMPLE 4

Synthesis of PrSPCl$_2$ and sulfurization

Equipment — 1 l. flask, stirrer, thermometer, reflux condensor, heat mantle, addition funnel

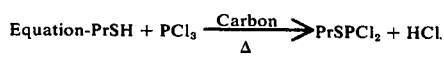

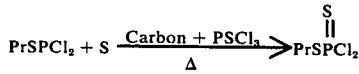

```
           Raw Materials:
1st   137.5 g    PCl₃ (1.0 mole)
       76.2 g    PrSH (1.0 mole)
       14.0 g    Darco KB carbon (14.0 g/mole)
2nd    20.0 g    PCl₃
       48.0 g    Sulfur
       20.0 g    PSCl₃
```

Procedure

Sweep flask with N$_2$ and charge PCl$_3$ (137.5 g) to flask Charge carbon to flask and PrSH to addition funnel. Heat to 55° C and add PrSH over 2½ hours. Heat to 75° C and cook for 1 hour. Analyze by GLC.

31.7 % (PrS)$_2$PCl
57.7 % PrSPCl$_2$
10.6 % PCl$_3$

Add 20.0 g PCl$_3$ and 48.0 g sulfur. Heat to reflux (118° C) temperature rose to 155° C after 2 hours. Cook 1 hour at 155° C analysis by GLC ratio of

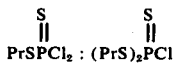

was 78 : 22.

Add 20 g PSCl$_3$ and cook 1 hour at 155° C ratio changed to 84:16. Distill at 1.55 mm Hg.

```
forecut = 46.4 g
Product cut = 140.1 g
A.I. = 96.2%        Crude yield (based on PrSH) = 67%
                    Net yield (based on PrSH) = 64.5%
```

EXAMPLE 5

PrSPCl$_2$ prepared from the reaction of PrSH and PCl$_3$ was sulfurized in 10 cycles. The conditions and results are summarized in Table I.

For each cycle the reactants were heated up to the cook temperature in the time indicated and cooked for the indicated period. After cooking the PSCl$_3$ and the PrSPSCl$_2$ were sequentially vacuum distilled off. After the first cycle the residue remaining acted as a heel for the next cycle.

The time for the reaction mixture to reach cook temperature decreased dramatically after the first cycle. This is believed to be due to the conditioning of the catalyst. In subsequent cycles the sulfurization reaction evidently proceeded more rapidly and thus refluxing subsided more quickly allowing the temperature to be raised to cook temperature in a shorter time.

The yields also increased substantially after the first cycle and also after the third cycle. The low yield in the eighth cycle is believed to be anomalous and probably due to the high pressure at which the product was distilled off (10 mm versus 5 mm for other cycles). It is believed that the presence of the residue from the previous cycle substantially enhances the recovery. The yield of greater than 100% in cycle 10 is believed to be due to the conversion of some of the residue of the previous cycle to product. The yields are reported in recovery of Active Ingredients (A.I.) based on the equivalents of PrS charged.

EXAMPLE 6

The final product, PrSP(S)Cl$_2$, was prepared from the S, PrSH, PCl$_3$ and PSCl$_3$ in a single vessel for ten cycles. The conditions, charges and results are summarized in Table 2. The K 310 charged in cycle 1 was the reaction product of PrSH and PCl$_3$ and was used to condition the carbon catalyst and provide a heel for subsequent cycles. Each subsequent cycle was initiated by the addition of the PrSH to the PCl$_3$ at a temperature of 20°–30° C. The evolution of HCl was instantaneous during the addition and ceased within 0.25 hours after the addition was complete. The sulfur and PSCl$_3$ was then added and the reaction mixture heated to the cook temperature. For each cycle after the first, some of the PSCl$_3$ was provided from recycling from the previous cycle and some additional was added. The activated carbon catalyst remained in the vessel after the first cycle and was present throughout succeeding cycles.

The cumulative product yield increased after each cycle. Thus at the end of the eleven cycles, the total recovery was 92.9% based on materials charged from the second cycle on.

EXAMPLE 7

All the reactants and the carbon catalyst were charged to the vessel at once. The mercaptan was added last to avoid its loss with the evolved HCl. The gas evolution was instantaneous upon the mercaptan evolution. The charges, conditions and results for the first four cycles are summarized in Table 3.

The yield increased substantially after both the first and second cycles. The time to reach cook temperature after the cessation of HCl evolution decreased substantially after the first cycle. The former effect is believed to be due to the presence of the distillation residue of the previous cycle while the later effect is believed to be due to the conditioning of the carbon catalyst.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

TABLE 1

Sulfurization of PrSPCl$_2$ in 10 Gallon Pfaudler Reactor

| Cycle | 1 | 2 | 3 | 4 | 5 | 6 | 7 | 8 | 9 | 10 |
|---|---|---|---|---|---|---|---|---|---|---|
| Charge, lbs. | | | | | | | | | | |
| PrSPCl$_2$ (composite) | 41.7 | 41.7 | 40 | 40 | 40 | 40 | 40 | 40 | 40 | 40 |
| PCl$_3$ | 2.0 | — | — | — | — | — | — | — | — | — |
| PSCl$_3$ | 10.0 | 13.2 | 1.5 | 12.0 | 12.0 | 12.0 | 12.0 | 12.0 | 12.0 | 12.0 |
| Sulfur | 9.6 | 6.4 | 9.5 | 7.6 | 7.6 | 7.6 | 7.6 | 7.6 | 7.6 | 7.6 |
| Carbon | 2.8 | recycle | recycle | recycle | recycle | recycle | recycle | recycle | recycle | recycle |
| Composition of nominal PrSPCl$_2$ | | | | | | | | | | |
| % PCl$_3$ | 20.2 | 16.4 | 16.4 | 16.4 | 16.4 | 15.5 | 15.5 | 16.3 | 14.4 | 14.0 |
| % PrSPCl$_2$ | 52.7 | 55.5 | 55.5 | 55.5 | 55.5 | 53.6 | 53.6 | 53.6 | 55.1 | 56.0 |
| % (PrS)$_2$PCl | 26.7 | 27.7 | 27.7 | 27.7 | 27.7 | 30.2 | 30.2 | 30.1 | 28.9 | 28.5 |
| Cook Temperature °C | 150° | 150° | 151° | 150° | 151° | 151° | 150° | 150° | 150° | 149° |
| Time to Cook Temp., Hrs. | 9.25 | 2.0 | 2.00 | 2.00 | 1.50 | 1.50 | 2.00 | 2.00 | 2.25 | 2.50 |
| Cook Period, Hrs. | 1.0 | 2.5 | 3.25 | 2.50 | 3.00 | 3.00 | 3.00 | 3.25 | 3.00 | 9.00 |
| PSCl$_3$ Distillation | | | | | | | | | | |
| Temperature °C | 22–44° | 24–74° | 37–95° | 24–99° | 19–100° | 21–95° | 23–100° | 20–116° | 25–97° | 26–71° |
| Pressure, mm Hg | 12–15 | 15 | 13–15 | 12–15 | 13.5–15 | 14–15 | 15 | 15 | 14.5 | 14.8 |
| Wt. Cut, Lbs. | 13.2 | 14.1 | 6.5 | 9.2 | 10.0 | 10.4 | 11.0 | 13.9 | 11 | 11 |
| Product Distillation | | | | | | | | | | |
| Temperature °C | 68–101° | 49–114° | 80–100° | 89–103° | 94–104° | 77–104° | 85–104° | 96–117° | 97–105° | 83–117° |
| Pressure, mm Hg | 5–6 | 5.0 | 4.5–5.0 | 4.5 | 5.1 | 4.0–5.0 | 5.0 | 10.0 | 5.3 | 5.2 |
| Wt. Cut, Lbs. | 28.2 | 39.5 | 38.0 | 51.0 | 48.5 | 44.5 | 45.0 | 33.0 | 47.2 | 66.0 |
| Product Composition: | | | | | | | | | | |
| % PSCl$_3$ | 2.08 | 2.31 | 3.30 | 2.79 | 2.92 | 2.69 | 2.45 | 8.51 | 6.56 | 13.74 |
| % PrSSPr | 2.21 | 1.39 | 4.27 | 2.55 | 0.85 | 1.01 | 1.26 | 1.16 | — | — |
| % PrSPsCl$_2$ | 95.5 | 94.8 | 89.2 | 89.5 | 95.1 | 93.4 | 93.5 | 89.0 | 89.4 | 83.0 |
| % (PrS)$_2$ PCl | 0.23 | 1.46 | 3.23 | 4.58 | 1.13 | 1.79 | 1.78 | 1.37 | 1.52 | 1.05 |
| Yield A.I. (on PrS equivalent) | 56.7 | 75.1 | 70.7 | 95.1 | 96.1 | 84.2 | 85.3 | 60.5 | 83.5 | 109.7 |

TABLE 2

Synthesis by "One-Pot" Process - Lab Scale

| Cycle | 1 | 2 | 3 | 4 | 5 |
|---|---|---|---|---|---|
| Charge: grams | | | | | |
| PrSH | | 375 | 380.8 | 381.0 | 381.0 |
| K-310 | 1042 | — | — | | |
| PCl$_3$ | 50 | 687.5 | 687.5 | 687.5 | 687.5 |
| Sulfur | 240 | 160 | 160 | 160 | 160 |
| Carbon | 70 | recycle | recycle | recycle | recycle |
| PSCl$_3$ | 250 | 381R | 359R | 360 | 360R |
| Gram Moles charge: | | | | | |
| PCl$_3$ | 1.993 | 5.000 | 5.000 | 5.000 | 5.000 |
| PrSPCl$_2$ | 2.440 | — | — | — | — |
| (PrS)$_2$PCl | 1.280 | — | — | — | — |
| Sulfur | 7.50 | 5.00 | 5.000 | 5.000 | 5.000 |
| PSCl$_3$ | 1.475 | 2.248 | 2.118 | 2.124 | 2.124 |
| PrSH | | 4.924 | 4.977 | 5.003 | 5.003 |
| Cook Conditions: | | | | | |
| Time, Hrs. | 1.0 | 1.08 | 2.25 | 1.83 | 2.00 |
| Temp. °C, Avg. | 150° | 152° | 152° | 152° | 154° |
| Distillation: | | | | | |
| PSCl$_3$ Cut, g | 381 | 359 | 302 | 299 | 271 |
| mm Hg | 5.0 | 4.9 | 5.0 | 15–20 | 10 |
| Vapor °C | 26–34° | 25–85° | 25–85° | 30–101° | 26–99° |
| Max Pot °C | 108° | 109° | 103° | 122° | 115° |
| K-500 Cut, g | 767 | 873 | 1038 | 947 | 1003 |
| mm Hg | 5.0 | 4.9 | 4.9 | 4.7 | 5 |
| Vapor °C | 97–101° | 96–102° | 93–102° | 101–106° | 99.5–105.5° |
| Max Pot °C | 140° | 139.5°13–9° | 140° | 140° | |
| Wt. PSCl$_3$ Out | 381 | 359 | 320 | 304 | 276 |
| Wt. PrSPSCl$_2$ Out | 718.8 | 829.8 | 988.5 | 906.4 | 957.4 |
| Product Analysis | | | | | |
| % PCl$_3$ | 0.77 | — | 0.9 | — | — |
| % PSCl$_3$ | 1.15 | 1.57 | 2.13 | 2.59 | 3.15 |
| % Pr$_2$S$_2$ | 3.62 | 2.61 | 1.56 | 0.97 | 1.21 |

TABLE 2-continued

Synthesis by "One-Pot" Process - Lab Scale

| | | | | | |
|---|---|---|---|---|---|
| %PrSPSCl$_2$ | 93.71 | 95.0 | 95.2 | 95.7 | 95.45 |
| % (PrS)$_2$PSCl | 0.75 | 0.85 | 0.15 | 0.45 | 0.19 |
| Yield of PrSPSCl$_2$,% | 68.8 | 80.6 | 95.0 | 86.7 | 91.6 |
| Cumulative % Yield on PrSH | | 80.6 | 87.9 | 87.5 | 88.5 |

| Cycle | 6 | 7 | 8 | 9 | 10 | 11 |
|---|---|---|---|---|---|---|
| Charge: grams | | | | | | |
| PrSH | 383.0 | 388.0 | 384.0 | 384.0 | 384.0 | 381.0 |
| K-310 | | | | | | |
| PCl$_3$ | 687.5 | 687.5 | 756.5 | 756.5 | 756.5 | 687.5 |
| Sulfur | 160 | 160 | 160 | 160 | 176 | 160 |
| Carbon | recycle | recycle | recycle | recycle | recycle | recycle |
| PSCl$_3$ | 360R | 360R | 324R | 324R | 324R | 360R |
| Gram moles Charge | | | | | | |
| PCl$_3$ | 5.000 | 5.000 | 5.502 | 5.502 | 5.502 | 5.000 |
| PrSPCl$_2$ | — | — | — | — | — | — |
| (PrS)$_2$PCl | — | — | — | — | — | — |
| Sulfur | 5.000 | 5.000 | 5.000 | 5.000 | 5.500 | 5.000 |
| PSCl$_3$ | 2.124 | 2.124 | 1.912 | 1.912 | 1.912 | 2.124 |
| PrSH | 5.030 | 5.095 | 5.043 | 5.043 | 5.043 | 5.135 |
| Cook Conditions: | | | | | | |
| Time, Hrs. | 2.00 | 2.50 | 2.50 | 2.50 | 2.50 | 2.50 |
| Temp. °C, Avg. | 151° | 153° | 152° | 151° | 152° | 152.5° |
| Distillation: | | | | | | |
| PSCl$_3$ Cut, g | 274 | 254 | 272 | 273 | 254 | 255 |
| mm Hg | 10 | 10 | 10 | 10 | 10–5 | 10 |
| Vapor °C | 27–99° | 27–99° | 25–99° | 28–99° | 27–80° | 25–99° |
| Max Pot °C | 112° | 112° | 112° | 111° | 106° | 111° |
| K-500 Cut, g | 1046 | 1048.5 | 1064 | 1113.5 | 1097 | 1138 |
| mm Hg | 5 | 4.8 | 5.0 | 4.90 | 5.0 | 4.8 |
| Vapor °C | 98–104.4° | 97–105° | 97–103° | 99–109° | 87–106° | 97.5–104.8° |
| Max Pot °C | 140° | 140° | 140° | 140° | 140° | 140° |
| Wt. PSCl$_3$ Out | 279 | 258 | 388.5 | 280 | 346.1 | 316.8 |
| Wt. PrSPSCl$_2$ Out | 987.2 | 983.7 | 987.5 | 1036.9 | 1020.9 | 1067.8 |
| Product Analysis | | | | | | |
| % PCl$_3$ | 0.29 | — | — | .12 | — | — |
| % PSCl$_3$ | 3.73 | 4.43 | 5.40 | 5.39 | 5.85 | 4.99 |
| % Pr$_2$S$_2$ | 1.14 | 1.20 | 1.30 | .69 | .36 | .64 |
| % PrSPSCl$_2$ | 94.4 | 93.8 | 92.8 | 93.12 | 93.06 | 93.83 |
| % (PrS)$_2$PSCl | 0.4 | 0.37 | 0.48 | 0.69 | 0.74 | 0.54 |
| Yield of PrSPSCl$_2$,% | 93.9 | 92.4 | 93.7 | 98.4 | 96.9 | 99.5 |
| Cumulative % Yield on PrSH | 89.6 | 90.1 | 90.6 | 91.6 | 92.2 | 92.9 |

R-Recycle PSCl$_3$ + Makeup
Note: HcL evoluton instantaneous during PrSH add. Evolution complete within 0.25 hrs after completing add. PrSH addition temp. 20–30° C

TABLE 3

PRODUCTION OF PrSP(S)Cl$_2$ by ONE-POT PROCESS ALL REACTANTS PRESENT AT PrSH ADDITIVE START

| Cycle NO. | 1 | 2 | 3 | 4 |
|---|---|---|---|---|
| Charge: | | | | |
| Carbon | 70 | Recycle | Recycle | Recycle |
| Sulfur | 240 | 160 | 160 | 160 |
| PSCl$_3$ | 250 | 360 | 360 | 360 |
| PCl$_3$ | 687.5 | 687.5 | 687.5 | 687.5 |
| n-PrSH | 385.0 | 380 | 382.5 | 383 |
| Mols Charge: | | | | |
| PCl$_3$ | 5.000 | 5.000 | 5.000 | 5.000 |
| PrSH | 5.056 | 5.062 | 5.023 | 5.030 |
| Sulfur | 7.500 | 5.000 | 5.000 | 5.000 |
| PSCl$_3$ | 1.475 | 2.124 | 2.124 | 2.124 |
| Temp. PrSH Add °C | 16–30° | 16–30° | 18–30° | 26–32° |
| Time PrSH Add, Hrs. | 0.33 | 0.25 | 0.33 | 0.25 |
| End PrSH to End HcL | 0.25 | 0.25 | 0.17 | 0.08 |
| End HCl to Cook | 1.67 | 0.58 | 0.67 | 0.67 |
| Time at Cook | 2.00 | 2.50 | 2.50 | 2.50 |
| Cook, Temp. °C | 153° | 152° | 152° | 153° |
| Wt. PSCl$_3$ Cut, g | 182 | 256.7 | 271.8 | 216.7 |
| Wt. Product Cut, g | 578.3 | 869 | 1068.9 | 976.7 |
| Analysis of Product | | | | |
| % PSCl$_3$ | 0.99 | 4.71 | 8.87 | 4.44 |
| % PrSSPr | 2.54 | 1.05 | 0.81 | 0.84 |
| % PrSPSCl$_2$ | 94.77 | 92.4 | 89.61 | 94.0 |
| % (PrS)$_2$PSCl | 0.76 | 0.45 | 0.72 | 0.74 |
| Yield, % on PrSH | 51.9 | 76.24 | 91.25 | 87.3 |
| Cumulative Yield, % | 51.9 | 63.9 | 73.0 | 76.5 |

What is claimed is:

1. A process for the production of S-alkyl phosphorodihaogenidodithioate comprising
   a. reacting a mercaptan with the formula RSH, wherein R is a straight chained or branched $C_1$–$C_{15}$ alkyl optionally substituted with halogen, alkoxy or alkylthio or cycloalkyl with 5 or 6 ring carbons, with sufficient PX$_3$ wherein X is Cl, Br or I to convert substantially all of the mercaptan to mono-, di- or tri-substituted trivalent phosphorous thioesters,
   b. reacting the thioesters and any excess phosphorous trihalide from step (a) with sufficient sulfur in the presence of a sulfurization catalyst to sulfurate any phosphorous trihalide present and to convert substantially all of the trivalent thioesters to pentavalent compounds,
   c. reacting the penta-valent di- and tri-substituted thioesters with sufficient PSX$_3$ to convert them to monosubstituted penta-valent thioesters,
   d. recycling the residue of di- and trisubstituted thioesters left after reaction with PSX$_3$ to the sulfurization reaction.

2. The process of claim 1, wherein R is $C_1$–$C_6$ alkyl and X is Cl or Br.

3. The process of claim 1, wherein step (a) is performed in the presence of the sulfurization catalyst.

4. The process of claim 3 wherein the whole process is conducted in a single vessel.

5. The process of claim 4 wherein all the necessary reactants are added at the start of the process.

6. The process of claim 1 wherein the sulfurization catalyst is recycled.

7. A process for the production of S-alkyl phosphorodichloridodithioate comprising a. reacting a $C_1$–$C_6$ alkyl mercaptan with sufficient phosphorous trichloride to convert substantially all of the mercaptan to trivalent phosphorous thioesters, b. reacting the thioesters so produced with sufficient sulfur in the presence of a sulfurization catalyst to convert all of the phosphorous present to the penta-valent state, c. holding the penta-valent thioesters at a sufficient temperature for a sufficient time with sufficient $PSCl_3$ to ensure that the major portion of the penta-valent thioesters is S-alkyl phosphorodichloridodithioate, d. sequentially removing the $PSCl_3$ and then the S-alkyl phosphorodichloridodithioate by vacuum distillation, and e. recycling the residue to the sulfurization reaction.

8. A process for the production of

wherein R is a straight chained or branched alkyl with up to 15 carbon atoms optionally substituted with halogen, alkoxy, alkylthio or cycloalkyl with 5 or 6 ring carbons comprising a. reacting at a temperature of less than about 75° C RSH with sufficient $PCl_3$ to convert substantially all of the RSH to $RSPCl_2$, $(RS)_2PCl$ and $(RS)_3P$ b. providing at least one mol of $PCl_3$ and/or $PSCl_3$ for each mole of $(RS)_2 PCl$ and two moles of $PCl_3$ and/or $PSCl_3$ for each mole of $(RS)_3P$ present, c. reacting the resultant mixture with sufficient sulfur in the presence of sulfurization catalyst to convert substantially all of the trivalent P present to the pentavalent state, d. holding the reacted mixture at a temperature of at least about 150° C for at least about 1 hour, e. removing the $PSCl_3$ and

by distillation and isolating the

f. using the distillation residue as a heel in the sulfurization reaction and, g. repeating the process.

9. The process of claim 8 wherein the entire process is conducted in a single vessel.

* * * * *